United States Patent [19]

Juneja

[11] Patent Number: 5,346,694
[45] Date of Patent: Sep. 13, 1994

[54] ACID STABLE GEL STICK ANTIPERSPIRANT COMPOSITIONS AND PROCESS FOR MAKING THEM

[75] Inventor: Prem S. Juneja, Cincinnati, Ohio

[73] Assignee: The Procter & Gamble Company, Cincinnati, Ohio

[21] Appl. No.: 47,255

[22] Filed: Apr. 14, 1993

Related U.S. Application Data

[63] Continuation of Ser. No. 696,376, May 6, 1991, abandoned.

[51] Int. Cl.$^5$ .................... A61K 7/34; A61K 7/36; A61K 7/38
[52] U.S. Cl. ................. 424/66; 424/DIG. 5; 424/67; 424/68
[58] Field of Search ............... 424/66, 68, DIG. 5

[56] References Cited

U.S. PATENT DOCUMENTS

| | | | |
|---|---|---|---|
| 4,154,816 | 5/1979 | Roehl et al. | 424/68 |
| 4,371,645 | 2/1983 | Mahaffey | 424/68 |
| 4,429,140 | 1/1984 | Murai et al. | 424/68 |
| 4,518,582 | 5/1985 | Schamper et al. | 424/68 |
| 4,719,102 | 1/1988 | Randhawa et al. | 424/68 |
| 4,722,835 | 2/1988 | Schamper et al. | 424/68 |
| 4,725,430 | 2/1988 | Schamper et al. | 424/68 |
| 4,743,444 | 5/1988 | McCall | 424/68 |
| 4,816,261 | 3/1989 | Luebbe et al. | 424/68 |

FOREIGN PATENT DOCUMENTS

| | | | |
|---|---|---|---|
| 0451002A2 | 10/1992 | European Pat. Off. | 424/68 |
| 0286522 | 12/1988 | Japan | 424/68 |
| 64-62377 | 3/1989 | Japan | 424/68 |

*Primary Examiner*—Dale R. Ore
*Attorney, Agent, or Firm*—Leonard W. Lewis

[57] ABSTRACT

Antiperspirant compositions in the form of gel sticks, which provide the user with excellent antiperspirant efficacy while exhibiting good stability, are disclosed. Specifically, the compositions have an acidic pH and include an antiperspirant active, a gelling agent which comprises dibenzylidene alditols, a solvent for the gelling agent, and a gelling agent stabilizer which is a basic metallic salt of an acid having a pKa of from about 3.8 to about 6.5 at 25° C, said salts being at least partially soluble in the composition, and said stabilizer being a salt selected from the group consisting of $C_4$–$C_6$ alkyl dicarboxylates, $C_6$–$C_8$ alkyl monocarboxylates, and substituted and unsubstituted benzoates, and mixtures thereof, wherein said gelling agent stabilizer does not contain amino or amido functionalities. Methods of preventing and controlling perspiration wetness using these compositions and of making the compositions are also disclosed.

23 Claims, No Drawings

ACID STABLE GEL STICK ANTIPERSPIRANT COMPOSITIONS AND PROCESS FOR MAKING THEM

This is a continuation of application Ser. No. 07/696,376, filed on May 6, 1991 now abandoned.

TECHNICAL FIELD

The present invention relates to antiperspirant compositions in the form of solid gel sticks. More particularly, the present invention relates to antiperspirant gel sticks containing dibenzylidene alditol gelling agent. The present invention further relates to a process for making antiperspirant gel stick compositions.

BACKGROUND OF THE INVENTION

There are three main types of antiperspirant stick formulations: compressed powder sticks, gel sticks, and wax sticks. While each of these formulation types may have advantages in certain usage situations, each also has disadvantages. For example, compressed powder sticks are often brittle and hard, leaving a cosmetically-unacceptable powder on the skin upon application. Wax-based formulations can also yield cosmetically-unacceptable products due to such factors as hardness, greasiness, and stickiness. The opacity of such wax sticks and the residue created by their use may also be aesthetically undesirable.

Gel-based sticks have several advantages over both compressed powder and wax sticks. For example, the gel sticks tend to leave little or no residue or dust on the skin. Gel sticks also provide a vehicle which glides easily over the skin's surface resulting in very easy and comfortable application of the product.

Unfortunately, the formulation of antiperspirant compositions in the form of effective and stable gel sticks is difficult. One critical ingredient in antiperspirant gel sticks is the gelling agent. Many known cosmetic gel sticks comprise gelled alcoholic solutions. Gelling agents, such as sodium stearate, have been used to form the gel. However, such gelling agents cannot be used in the presence of acidic antiperspirant active salts, due to interactions with the antiperspirant active.

Gelling agents which are more useful in the preparation of antiperspirant gel sticks are the dibenzylidene alditols, such as dibenzylidene sorbitol (DBS). See, for example, U.S. Pat. Nos. 4,154,816, Roehl et al., issued May 15, 1979; 4,816,261, Luebbe et al., issued Mar. 28, 1989; and 4,743,444, McCall, issued May 10, 1988. Various substituted dibenzylidene alditol gelling agents can also be used in antiperspirant gel sticks.

Japanese Published Application 64-62377, Kao, published Mar. 8, 1989, describes fluorinated dibenzylidene polyhydric alcohol derivatives which are effective gelling agents for cosmetic compositions containing a wide range of organic solvents.

U.S. Pat. No. 4,429,140, Murai et al., issued Jan. 31, 1984, discloses a method for producing DBS and its derivatives. Disclosed DBS derivatives include those where the benzene ring is substituted with from 1 to 3 lower alkyl groups, lower alkoxy groups, halogen atoms or nitro groups.

U.S. Pat. No. 4,371,645, Mahaffey, issued Feb. 1, 1983, describes plastic compositions which include DBS derivatives for improved transparency. These DBS derivatives must include a chlorine or bromine substituent in the meta and/or para positions and may also include lower alkyl, hydroxy, methoxy, mono- or dialkyl amino, or fluorine substituents. Di (para-chloro) DBS, di(para-fluoro) DBS, and di(para-methoxy) DBS are all specifically disclosed.

European Pat. Application 0286522, Roquette Freres, published Dec. 1, 1988, describes a process for making high purity alditol diacetals. Para-chloro DBS is disclosed.

Gelling agents found to be particularly useful for antiperspirant gel sticks are disclosed in U.S. Pat. No. application Ser. No. 07/505,807, Oh, Juneja, and Connor, filed Apr. 6, 1990. This application discloses substituted dibenzylidene alditols that are derivatized at the meta position of the benzene rings. Exemplary compounds include di (meta-fluoro) DBS and di(meta-chloro) DBS. These meta-substituted dibenzylidene alditols have improved stability in acidic conditions.

During processing and manufacture of antiperspirant gel sticks containing dibenzylidene alditol gelling agents, it is necessary to solubilize the gelling agent in a solvent, typically a monohydric or polyhydric alcohol. In order to do this, it is necessary to heat the ingredients to a temperature which is high enough to induce solubilization and which is also above the gel point of the gelling agent/solvent solution. Unfortunately, the relatively high temperatures required tend to cause the gelling agents to degrade in the presence of antiperspirant actives or other acidic materials. This is often exascerbated by practical matters during processing which often require that the composition be held at such high temperature, above the gel point, before packaging, and consequently cooling to form the gel, can be completed. Degradation can continue even at lower temperatures, throughout the life of the product. Accordingly, there is a need to provide antiperspirant gel stick compositions containing benzylidene alditol gelling agents which can exhibit improved gel stability. There is further a need to provide a process for making antiperspirant gel stick compositions by which decomposition of the gelling agent in the presence of acidic materials can be reduced.

It has been attempted in the past to meet these objects. For example, in U.S. Pat. Nos. 4,722,835, Schamper et al., issued Feb. 2, 1988, 4,719,102, issued Jan. 12, 1988, Randhawa et al., 4,518,582, Schamper et al., issued May 21, 1985, and 4,725,430, Schamper et al., issued Feb. 16, 1988 it is proposed in specific compositions to incorporate certain basic metallic salts as stabilizing agents into antiperspirant sticks utilizing a dibenzylidene monosorbitol acetal gelling agent. The basic metallic salt added as a gelling agent stabilizing agents include magnesium sulfate, zinc acetate, zinc oxide, calcium acetate, magnesium oxide, calcium carbonate, calcium hydroxide, magnesium carbonate, sodium carbonate, zinc and potassium carbonate. U.S. Pat. No. 4,518,582 also discloses the use of hexamethylenetetramine as a gel stabilizer and 4,725,430 also discloses an N-(2-hydroxyethyl) acetamide. Whereas these compositions are said to have increased gelling agent stability, the stabilizers disclosed have certain disadvantages which limit their effectiveness or ability to be incorporated into viable consumer products, such as off-odors, compatibility with other ingredients (especially at acidic pH), compatibility with the skin, etc.

The present invention provides specific gelling agent stabilizers to be used in dibenzylidene alditol-containing antiperspirant gel compositions which can provide improved gelling agent efficiency, improved gel stability of the composition, and reduced gelling agent interaction with acidic materials, e.g., antiperspirant active, in processing and storage. Additionally, the gelling agent stabilizers do not impart undesirable off-odors to the product and are compatible with other ingredients in the composition. The present invention also provides a method of making such compositions.

SUMMARY OF THE INVENTION

The present invention provides for solid antiperspirant compositions in gel stick form, having acidic pHs, comprising:
(a) from about 0.5% to about 35% of an antiperspirant active;
(b) from about 0.5% to about 10% of a gelling agent selected from the group consisting of substituted and unsubstituted dibenzylidene alditols (such as sorbitols, xylitols, and ribitols), and mixtures thereof;
(c) from about 5% to about 98% of a solvent for said gelling agent, preferably comprising a solvent material selected from the group consisting of monohydric and polyhydric alcohols, and mixtures thereof; and
(d) from about 0.05% to about 5%, by weight, of a gelling agent stabilizer, said stabilizer being a basic metallic salt of an acid having a pKa of from about 3.8 to about 6.5 at 25° C., said salt being at least partially soluble in the composition, and said stabilizer being selected from the group consisting of $C_4$–$C_6$ dicarboxylate salts, $C_6$–$C_8$ monocarboxylate salts, and substituted or unsubstituted benzoate salts, and mixtures thereof, wherein said gelling agent stabilizer does not contain amino or amido functionalities.

DETAILED DESCRIPTION OF THE INVENTION

The solid antiperspirant compositions encompassed by the present invention are in the form of gel sticks. These sticks have a suitable hardness such that they deposit an effective amount of antiperspirant material on the skin during normal use, while maintaining dimensional stability upon use and storage. Hardness of sticks can be determined by a variety of methods, including American Society for Testing and Materials (ASTM) Method D-5. This method involves the use of a needle or polished cone of particular weight and dimension, which is allowed to travel downward through the stick material for a predetermined period of time. The distance travelled by the needle or cone is a relative measure of stick hardness. Using Method D-5, with an ASTM-D1321 arrowhead-type penetration needle (Model 13-401-10, sold by Fischer Scientific Co.), weighing 50 grams, and a Model 13-399-10 Penetrometer (sold by Fischer Scientific Co.), the stick compositions of the present invention preferably have an average penetration value of from about 60 to about 200 measured in units of tenths of a millimeter, more preferably from about 100 to about 160, over a period of 5 seconds at ambient temperature. These values represent an average penetration for sticks within a given production batch, since such penetration values may vary from stick to stick within the batch.

The stick compositions of the present invention, by virtue of their incorporation of antiperspirant actives, are acidic in nature. Specifically, they have an apparent pH of from about 1.5 to about 4. The term "apparent pH" is used herein since the compositions are generally non-aqueous and, therefore, the pH of the composition is being measured in a non-aqueous system. Specifically, the pH is determined by melting the stick and measuring its pH at 25° C. using a standard pH meter. If the stick is melted at a relatively high temperature (for example, about 120° C. for about 1 hour), it will not resolidify upon cooling and the pH at 25° C. can be easily measured. Under these conditions, the apparent pH of the compositions of the present invention should be from about 1.5 to about 4.

All parts, percentages and ratios specified herein are by weight, unless otherwise specified.

The required, as well as the optional, components of the present invention are described in detail below.

Gelling Agent

The compositions of the present invention include from about 0.5% to about 10%, preferably from about 2% to about 5%, most preferably from about 2% to about 3.5%, of a specifically defined gelling agent component. This gelling agent component is a dibenzylidene alditol (for example, a sorbitol, xylitol or ribitol) which can be substituted or unsubstituted. Preferred are dibenzylidene sorbitol (DBS) and DBS derivatives.

To aid in understanding the present invention, the following are diagrams of dibenzylidene sorbitol, and dibenzylidene xylitol with the ortho, meta and para positions indicated.

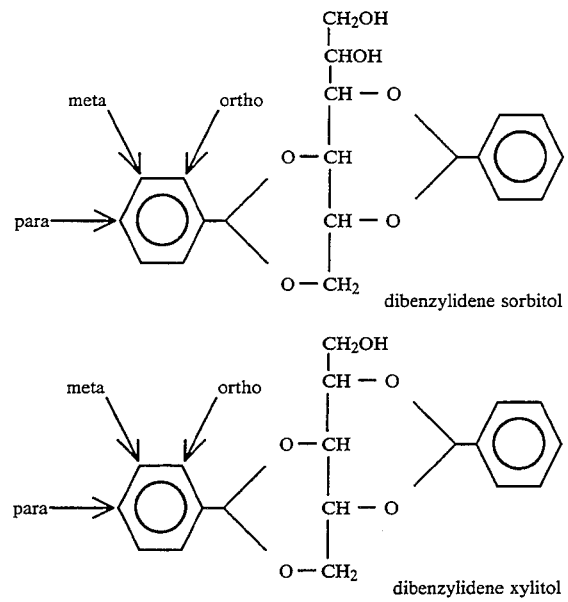

dibenzylidene sorbitol dibenzylidene xylitol

Dibenzylidene ribitol is structurally similar to dibenzylidene xylitol, except it is based on ribitol rather than xylitol.

Other unsubstituted dibenzylidene alditols include dibenzylidene xylitol (DBX) and dibenzylidene ribitol (DBR).

The preferred substituted dibenzylidene alditols are substituted with one or more electron withdrawing groups. It is especially preferred for the substituents that are electron withdrawing groups to be located at the meta position, although substituents can also be located at the para or ortho positions. Likewise, substituents can be located at a combination of the meta and para, meta and ortho, or para and ortho positions. The preferred electron withdrawing substituents include —$CH_2F$, —$CH_2Cl$, —F, —Cl, —Br, —I, and —CH=$CHNO_2$. Preferably, at least one of the electron withdrawing substituents is located at the meta position of the benzene ring. Multiple substituents (including those not on the list) may be utilized in these preferred gelling agents as long as at least one from the list is located at the meta position. Most preferably, the alditol is sorbitol.

In other preferred gelling agents, at least one of certain substituents are located at the meta or para position of the benzene ring. Once again, more than one of these substituents (or even substituents not on the list) may be included in a particular molecule, as long as at least one from the list is positioned at the meta or para position. These substituents include:

—$NO_2$, —$NH_3$, —$NR_3$, —$PR_3$, —$PH_3$, —$SR_2$,
—$CF_3$, —$CCl_3$, —$CHF_2$,
—$CHCl_2$, —CHClF, —$CCl_2F$, —$CF_2Cl$, —$SO_3H$,
—$SO_3R$, —$CO_2H$, —$CO_2R$,
—$CONH_2$, —CHO, —COR, and —C≡N, wherein R is $C_1$-$C_4$ alkyl.

Especially preferred substituted gelling agents for use in the present invention include the following substituents at the meta position: —$CH_2F$, —$CH_2Cl$, —F, —Cl, —Br, —I, and —CH=$CHNO_2$; particularly preferred are the —F and —Cl substituents. It is preferred that this meta substitution be the only substitution on the benzene ring. The substituents described herein will generally be found on both benzene rings of the compound. Particularly preferred are di(meta-fluorobenzylidene) sorbitol and di(meta-chlorobenzylidene) sorbitol.

The substituents listed above provide gelling agents which exhibit good stability in the acid environment of an antiperspirant composition. A preferred sub-group of these substituents are those which have smaller molecular sizes since they tend to generally provide stronger gels. Thus, for example, the gel provided by a fluorine or chlorine substituted compound tends to be stronger than one provided by a trifluoromethyl substituted compound. It is also preferred that the gelling agents utilized in the compositions of the present invention have a high purity. For example, they should be substantially free of para-toluene sulfonic acid or any other catalyst used in their synthesis as well as any salt forms (e.g., sodium) of these gelling agents. The presence of such impurities may tend to weaken the gel formed.

Mixtures of the gelling agents specified herein may be used in the compositions of the present invention.

Gelling agents that can be used herein are generally disclosed in British Patent 1,291,819, published Oct. 4, 1972, U.S. Pat. Nos. 4,518,582, Schamper et al., issued May 28, 1985, 4,154,816, Roehl et al., issued May 15, 1979; 4,816,261, Luebbe et al., issued Mar. 28, 1989; 4,743,444, McCall, issued May 10, 1988, and 4,429,140, Murai et al., issued Jan. 31, 1984, all of which are incorporated by reference herein. The preferred unsubstituted DBS is commercially available, for example, as GELL-ALL-D (manufactured by New Japan Chemical Co., Ltd.) and MILLITHIX 925 (manufactured by Milliken Chemical, Division of Milliken & Company).

The preferred meta-substituted gelling agents are generally formed by converting a meta-substituted benzaldehyde to the corresponding meta-substituted DBS using a reaction such as that taught in European Pat. Application 0286522, Roquette Freres, published Dec. 1, 1988, incorporated herein by reference. As specific examples, the synthesis of meta-fluoro DBS and meta-chloro DBS is described below.

A solution of D-sorbitol (1006 g; 5.52 mol) in 3000 mL of distilled water, m-fluorobenzaldehyde (1240 g; 9.99 mol), and p-toluenesulfonic acid monohydrate (1310 g; 6.87 mol) is stirred at 30° C. for 21 h. The resulting suspension is neutralized to a pH of 7.0–7.5 with an aqueous 10% NaOH solution, and the white precipitate is collected by filtration. The solid is then suspended and stirred, in succession, in reagent grade acetone (3×10.0 L), and hot (60° C.) distilled water (3×10.0 L), collected, and dried in vacuo at 50° C. to give 1113 g (47%) of purified di(meta-fluoro) DBS.

Di(meta-chloro) DBS is synthesized using a similar procedure, except that meta-chloro benzyaldehyde is used in place of meta-fluoro benzaldehyde.

Para-substituted compounds used in the present invention are synthesized using a similar procedure, except that para-substituted benzyaldehyde is utilized as the starting material. The general method for synthesizing substituted dibenzylidene xylitols and substituted dibenzylidene ribitols is taught in Japanese Published Application 64-62377, Kao, published Mar. 8, 1989, and U.S. Pat. No. 4,429,140, Murai et al., issued Jan. 31, 1984, both incorporated herein by reference. Ortho-substituted compounds can be made in a similar manner.

Antiperspirant Active

The compositions of the present invention also contain from about 0.5% to about 35%, preferably from about 5% to about 35%, more preferably from about 5% to about 25%, of an antiperspirant active. The antiperspirant actives hereof are antiperspirant active astringent metal salts and astringent complexes of such salts. The active may be incorporated either in solubilized or particulate form. If a clear or translucent stick composition is desired, the composition must comprise an antiperspirant active which can exist in solubilized form in the solvent system. This solvent system can be the same solvent used to form the base matrix with the gelling agent. Alternately, other solvents can be used as the antiperspirant active solvent in addition to the gelling agent solvent. These weight percentages are calculated on an anhydrous metal salt basis (exclusive of glycine, the salts of glycine, or other complexing agents). If used in particulate form, the material preferably has a particle size of from about 1 to about 100 microns, preferably from about 1 to about 50 microns. They may be impalpable or microspherical in form and, preferably, have a high bulk density (e.g., greater than about 0.7 g/$cm^3$). Such materials include, for example, many aluminum or zirconium astringent salts or complexes and are well known in the antiperspirant art.

Any aluminum astringent antiperspirant salt or aluminum and/or zirconium astringent complex can be employed herein. Salts useful as astringent antiperspirant salts or as components of astringent complexes include aluminum halides, aluminum hydroxyhalides, zirconyl oxyhalides, zirconyl hydroxyhalides, and mixtures of these materials.

Aluminum salts of this type include aluminum chloride and the aluminum hydroxyhalides having the general formula $Al_2(OH)_xQy \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. Nos. 3,887,692, Gilman, issued Jun. 3, 1975, and 3,904,741, Jones and Rubino, issued Sept. 9, 1975, incorporated herein by reference.

Zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to O, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal :Cl ratio of from about 0.73 to about 1.93.

Preferred ZAG complexes are formed by
(A) co-dissolving in water
(1) one part $Al_2(OH)_{6-m}Q_m$, wherein Q is an anion selected from the group consisting of chloride, bromide and iodide, and m is a number from about 0.8 to about 2.0;
(2) x parts $ZrO(OH))_{2-a}Q_a.nH_2O$, where Q is chloride, bromide or iodide; where a is from about 1 to about 2; where n is from about 1 to about 8; and where x has a value of from about 0.16 to about 1.2;
(3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) co-drying the resultant mixture to a friable solid: and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula $[Al_2(OH)_4Cl][H_2CNH_2—COOH]$. All of these patents are incorporated herein by reference.

Of all the above types of antiperspirant actives, preferred compounds include the 5/6 basic aluminum salts of the empirical formula $Al_2(OH)_5Cl.2H_2O$, such compounds being commonly referred to as aluminum chlorohydrates ("ACH"); mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Solubilized antiperspirant actives which may be utilized in the present invention are also well known in the art, and include the actives described above. Compositions containing solubilized antiperspirant active utilize solvents, such as monohydric or polyhydric alcohols or water, to solubilize the anti perspirant active before it is incorporated into the product. Example of actives for such use are taught, for example, in U.S. Pat. No. 4,137,306, Rubino, issued Jan. 30, 1979, U.S. patent application Ser. No. 370,559, Smith and Ward, filed Jun. 23, 1989, and European Published Application 0295070, published Dec. 14, 1988, all of which are incorporated by reference herein. ACH is the preferred type of active for compositions containing solubilized antiperspirant active.

Examples of especially preferred actives include improved efficacy ACH (IACH) and improved efficacy ZAG (IZAG). The enhanced efficacy is due to improved molecular distribution. Such materials are described in U.S. Pat. No. 4,359,456, Gosling et al., issued Nov. 16, 1982; European Patent Application Publication No. 6,739, to Unilever Limited, published Jan. 9, 1980; European Pat. Application Publication No. 183,171, to Armour Pharmaceutical Company, published Jun. 4, 1986; British Pat. Specification No. 2,048,229, The Gillette Company, published Dec. 10, 1980; European Pat. Application Publication No. 191,628, to Unilever PLC, published Aug. 20, 1986; British patent specification No. 2,144,992, The Gillette Company, published Mar. 20, 1985; European Pat. Application Publication No. 7,191, to Unilever Limited, published Jan. 23, 1980; all incorporated by reference herein in its entirety; as well as previously incorporated U.S. Ser. No. 370,559, filed Jun. 23, 1989 and European Pat. No. 0295070.

Solvent

The compositions of the present invention also include from about 5% to about 98%, preferably from about 7% to about 90%, most preferably from about 60% to about 85%, of a solvent for the gelling agent. The solvent forms the base matrix of the solid stick when combined with the gelling agent. As will be appreciated by those skilled in the art, the selection of a particular solvent will depend upon the characteristics of the stick desired. For example, the solvent can also solubilize the antiperspirant active component in formulations having solubilized antiperspirant active material. For another example, the solvent may be selected to provide such cosmetic benefits as emolliency when applied to the skin. Solvents useful herein include, for example, monohydric alcohols (particularly lower monohydric alcohols), polyhydric alcohols, and mixtures thereof. Water may also be included as part of the solvent. However, the solvent will generally comprise water at levels no greater than about 5%, by weight, of the final composition.

Examples of solvents which may be utilized in the present invention include liquid polyethylene glycols (e.g., diethylene glycol, triethylene glycol), liquid polypropylene glycols (e.g., dipropylene glycol, tripropylene glycol, triethylene glycol ), liquid polypropylene polyethylene glycol copolymers, water, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are polypropylene polyethylene glycol copolymers, such as PPG-5-buteth-7.

These solvents are fully described, for example, in U.S. Pat. No. 4,518,582, Schamper et al., issued May 21, 1985, and European Published Application 107,330, Luebbe et al., published May 2, 1984, both incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene glycol, and mixtures thereof.

Gelling Agent Stabilizer

The present compositions contain, as an essential ingredient, an effective amount of a gelling agent stabilizer for enhancing stability of the gelling agent in the acidic environment of the antiperspirant composition. In general, the compositions will contain from about 0.05% to about 5%, by weight, of the stabilizer, preferably from about 0.1% to about 3%, more preferably from about 0.5% to about 2%.

The gelling agent stabilizers are basic metallic salts of $C_4$–$C_6$ alkyl dicarboxylic acids, $C_6$–$C_8$ alkyl monocarboxylic acids, and substituted and unsubstituted benzoic acids. The alkyl radicals of the $C_4$–$C_6$ alkyl dicarboxylates and the $C_6$–$C_8$ alkyl monocarboxylates should be saturated and unsubstituted. The gelling agent stabilizers for use herein are basic metallic salts of weak acids having a pKa of from about 3.8 to about 6.5 at ambient temperature, preferably from about 3.8 to about 6.0. The gelling agent stabilizers hereof are further characterized by the absence of amino and amido functionalities. The stabilizer must be in at least a partially solubilized state in the antiperspirant composition in order to neutralize strong acids that are present. Such strong acids typically are present as residual impurities in the solvent or gelling agent, or are generated from the antiperspirant active. Without being limited to any particular theory, it is believed that the presence of strong acids in the gel sticks, in combination with even small amounts of water, catalyze decomposition of the dibenzylidene alditol gelling agent. The stabilizers hereof neutralize such strong acids by reaction to form a weak acid and a metallic salt of the strong acid. These weak acids are poor proton donors, and are believed to not significantly destabilize the gelling agent. The precise level of solubilized stabilizer is not critical, so long as an effective amount is present to inhibit decomposition of the gelling agent. Enhanced stability of the composition can be determined over time by comparison of products made with the gel stabilizer of the present invention versus those made without it. A variety of appropriate analytical methods known in the art, including, for example, quantitavely analyzing the amount of gelling agent in the composition by high performance (pressure) liquid chromatography (HPLC), comparative hardness of the gel, and measurement of gel conversion to the liquid state. These determinations can be accelerated by increasing storage temperature of the composition. The stabilizer is preferably well distributed throughout the antiperspirant composition.

For clear or translucent antiperspirant gel stick compositions, the gelling agent stabilizer present in the composition should be fully soluble in the composition, in order to minimize refraction of light. For opaque antiperspirant gel stick compositions containing the antiperspirant active in particulate form, the stabilizer need only be partly soluble in the composition, although stabilizers that are completely soluble in the composition are preferred.

Suitable salt forming cations include sodium, potassium, lithium, magnesium, calcium, and zinc. Preferred are sodium, potassium, magnesium, and calcium, more preferred are sodium, potassium, and calcium. Most preferred are potassium and sodium.

The $C_4$–$C_6$ dicarboxylate and $C_6$–$C_8$ monocarboxylate salts for use as gelling agent stabilizers hereof include succinate, glutarate, adipate, hexanoate, heptanoate, and octanoate salts, and mixtures thereof. More specific examples of the $C_6$–$C_8$ monocarboxylate stabilizing agents include n-hexanoate, n-heptanoate, and n-octanoate.

Examples of unsubstituted and substituted benzoate stabilizing agents include benzoate salts (unsubstituted) and derivatives of the benzoate salts (substituted). Substituted benzoate salts include ,mono-halogen, mono-, di-, and tri-hydroxy methyl- and ethyl-, and mono- and di-methoxy-substituted derivatives. Specific examples of benzoate derivatives include 3-fluorobenzoate, 3-hydroxybenzoate, 2-methylbenzoate, 4-bromobenzoate, 4-chlorobenzoate, 2,5-dimethylbenzoate, 2-methoxybenzoate, 3methoxybenzoate, 4-fluorobenzoate, 2,4-dimethylbenzoate, 3-methylbenzoate, 3,5-dimethylbenzoate, 3,4,5-trihydroxybenzoate, 4-ethylbenzoate, 4-methyl benzoate, and 3,4-dimethylbenzoate. The substituent or substituents substituted onto the benzoate should not change the pKa of the corresponding acid outside the above range and should not cause the benzoate to become odoriferous. Additionally, the substituted benzoate should be compatible with the other ingredients in the composition and be suitable for application to the skin.

Preferred stabilizers are unsubstituted benzoate, succinate, and octanoate salts. Especially preferred are benzoate and octanoate salts, particularly the sodium and potassium salts thereof.

Optional Components

The compositions of the present invention may also contain other optional components which modify the physical characteristics of the compositions or serve as "active" components when deposited on the skin in addition to the antiperspirant material. Optional components useful herein are described in the following documents, all incorporated by reference herein: U.S. Pat. No. 4,049,792, Elsnau, issued Sep. 20, 1977; Canadian Patent 1,164,347, Beckmeyer et al., issued Mar. 27, 1984; European Patent Application 117,070, May, published Aug. 29, 1984; and Geria, "Formulation of Stick Antiperspirants and Deodorants", Cosmetics & Toiletries, 99:55–60 (1984).

The specific non-active components that may be useful will depend upon the characteristics desired for the particular stick composition. Such components include, for example, emollients, humectants, hardeners (e.g., wax), fillers and particulate materials, colorants, perfumes, and emulsifiers. As used herein, "particulate materials" are those materials, including colloidal dispersions, that neither dissolve in the composition components nor melt during the manufacture of the stick.

The compositions of the present invention may contain from about 1% to about 40% of one or more emollients. These emollients may have an intermediate polarity, such as the ethyl, isopropyl and n-butyl diesters of adipic, phthalic and sebacic acids. Preferred examples of such emollients include di-n-butyl phthalate, diethyl sebacate, diisopropyl adipate and ethyl carbomethyl phthalate, all of which are disclosed in U.S. Pat. No. 4,045,548, Luedders et al., issued Aug. 30, 1977, which is incorporated by reference herein. Other useful emollients include $C_{12}$–$C_{15}$ alcohol benzoates (commercially available as Finsolv from Finetex, Inc.). Useful emollients also include fatty alcohols, such as cetyl and stearyl alcohols, which (if used) will preferably be present at levels of from about 1% to about 10%, more preferably about 1% to about 5%. The compositions of the present invention may also include non-polar emollients, such as volatile silicone oils, non-polar nonvolatile emollients, and mixtures thereof. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the antiperspirant stick compositions disclosed herein:

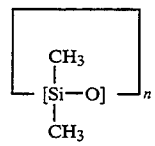

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C., while cyclic materials typically have viscosities of less than about 10 centistokes. A description of various volatile silicone oils is found in Todd et al., "Volatile Silicone Fluids for Cosmetics", Cosmetic & Toiletries, 91, pages 27–32 (1976), the disclosures of which are incorporated by reference herein.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by Union Carbide Corp.); SF 1202 (manufactured by General Electric); and SWS-03314 (manufactured by SWS Silicones, Inc. ).

Non-volatile silicone oils useful as emollient materials include polyalkylsiloxanes, polyarylsiloxanes and polyethersiloxane copolymers. The essentially nonvolatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 2 to about 400 centistokes at 25° C. Such polyalkyl siloxanes include the Viscasil series (sold by General Electric Company) and the Dow Corning 200 series (sold by Dow Corning Corp.). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corp.). Useful polyether siloxane copolymers include, for example, a polyoxyalkylene ether copolymer having a viscosity of about 1200 to 1500 centistokes at 25° C. Such a fluid is available as SF1066 organosilicone surfactant (sold by General Electric Company).

Polysiloxane ethylene glycol ether copolymers are preferred copolymers for use in the present compositions.

The compositions of the present invention may contain a processing aid. These components act to reduce the gel formation temperature of the composition or reduce the melting temperature of the gellant. Examples of such materials are taught in U.S. Pat. No. 4,719,102, Randhawa et al., issued Jan. 12, 1988, incorporated herein by reference, and include, among others, propylene carbonate, butyrolactone, caprolactone, and mixtures thereof. More preferred processing aids are cosolvents, used in combination with the solvents described above (e.g., monohydric and polyhydric alcohols), which are 2-oxazolidinone compounds having a $C_1$–$C_4$ alkyl radical substituted at the 3 position of the heterocyclic ring, or a mixture of such compounds. This cosolvent should be miscible with the solvent. The gelling agent should also be more soluble in the cosolvent than in said other solvent in order for processing temperature of the compositions to be reduced. The 2-oxazolidinone cosolvent will typically be present in the composition at a level of about 0.5% to about 40%, by weight, of the composition, preferably from about 1% to about 25%, more preferably from about 5% to about 15%. The weight ratio of monohydric and polyhydric alcohol solvent to said 2-oxazolidinone is preferably from about 1:1 to about 50:1, more preferably from about 3:1 to about 20:1, and a weight ratio of gelling agent to said 2-oxazolidinone is preferably from about 0.05:1 to about 2:1, more preferably from about 0.1:1 to about 1: 1.

In general the 2-oxazolidinone compound has the formula:

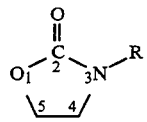

wherein the radical R at the 3 position is a $C_1$–$C_4$ alkyl, preferably a $C_1$–$C_2$ alkyl, more preferably $C_1$ (i.e., methyl ). The preferred compounds have hydrogens at the 4 and 5 positions, and are identified as 3-($C_1$–$C_4$ alkyl)-2-oxazolidinone. More preferred are 3-($C_1$–$C_2$ alkyl)-2-oxazolidinones. Most preferred is 3-methyl-2-oxazolidinone. The compound may have substituents located at the 4 and 5 positions of the heterocyclic ring instead of hydrogen. Preferably, if used, such substituents are lower chain alkyls, e.g., $C_1$–$C_4$ alkyl, preferably $C_1$–$C_2$ alkyl, more preferably methyl. Other substituents can be present which do not cause the compound to be immiscible with other solvents or reduce solubility of the gelling agent in it to less than in the mono- and polyhydric alcohol solvent. Also, the compound should remain stable against decomposition in the processing of and under the typical storage and use conditions of the gel stick compositions.

The compositions of the present invention may also contain from about 0.5% to about 10% of an inert filler material. Suitable filler materials include colloidal silica (such as Cab-O-Sil, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987, incorporated herein by reference.

The compositions of the present invention may also include perfumes, emulsifiers and coloring agents well known in the art, at levels of from about 0.1% to about 5%.

In addition to the antiperspirant actives, discussed above, the antiperspirant sticks of the present invention may also contain a safe and effective amount of one or more additional components which are meant to be deposited upon human tissue. Such active components include astringents, bacteriostats, fungistats, pigments, dyes, colorants, perfumes, emollients, ultra-violet absorbers, and mixtures thereof. These components must be stable in the formulation of the instant invention. A "safe and effective" amount of such active components is that amount which yields the desired benefit at a reasonable benefit/risk ratio for human usage. Various active components among those useful in the present invention are described in U.S. Pat. No. 4,226,889, Yuhas, issued Oct. 7, 1980, incorporated by reference herein.

The present invention further provides a process for making antiperspirant gel stick compositions wherein decomposition of the gelling agent during processing can be reduced. Additionally, improved gel stability of the final composition can also be obtained.

More specifically, provided is an improved process for making an antiperspirant gel stick composition, having acidic pH, containing a solvent, substituted or unsubstituted dibenzylidene alditol gelling agent, and an antiperspirant active, said process comprising solubilizing the gelling agent in the solvent at elevated temperature to form a solution and subsequently cooling the solution to form a gel, wherein the improvement comprises incorporating into the solvent an effective amount of a gelling agent stabilizer for enhancing gelling agent stability, said stabilizer being a basic metallic salt of an acid having pKa of from about 3.8 to about 6.5 at ambient temperature, said salt being selected from the group consisting of $C_4$–$C_6$ alkyl dicarboxylates, $C_6$–$C_8$ alkyl monocarboxylates, and substitut d unsubstituted benzoates, and mixtures thereof, wherein the gel stabilizer does not contain amino or amido functionalities.

Preferably, the gel stabilizer is added to the solvent prior to heating the solvent to solubilize the gelling agent, and also preferably prior to addition of the antiperspirant active to the solvent. The term "solvent", as used in this processing context, includes any material being used which is capable of solubilizing the gelling agent, or in which the gelling agent can exist in solubilized form, including processing aids which can be used as cosolvents, as described above.

This process can provide antiperspirant gel stick compositions with improved gel shelf-stability. Additionally, this process can provide improved gelling agent stability during processing, and consequently improved initial gel stick compositions and improved gelling agent efficiency. This process is especially beneficial in conditions wherein it is required to hold the composition at elevated temperatures, e.g., above the gel point, such as in anticipation of packaging and subsequent cooling to form the gel.

In a preferred process, the antiperspirant gel stick composition is made by:
(a) preparing a solution containing from about 0.5% to about 10%, by weight of the final composition, of a substituted or unsubstituted dibenzylidene alditol gelling agent, a solvent for said gelling agent, and from about 0.05% to about 5%, by weight of the final composition, of a gelling agent stabilizer as defined herein, said stabilizer being at least partially soluble in the solution of solvent and gelling agent;

(b) mixing an antiperspirant active into said solution; and (c) cooling said solution to form a gel; wherein said gel has an average penetration value of from about 60 to about 200 tenths of a millimeter at ambient temperature.

Preferably, level and selection of the solvent, gelling agent stabilizer, and antiperspirant active in the final composition are as previously described.

In general, it will be required to heat the solvent, preferably comprising a mono- or polyhydric alcohol, or mixture thereof, to about 70° C. to about 150° C. in order for the gelling agent to dissolve.

Consistent with the above, the compositions of this invention may be made by techniques generally known to those skilled in the art. Such techniques are described in "Gels and Sticks Formulary", Cosmetics & Toiletries, 99, 77–84 (1984), incorporated by reference herein. After the antiperspirant active and optional components are added, the solution is poured into stick molds. A solid gel forms upon cooling. As the stick composition may solidify rapidly upon cooling, care should be taken so as to maintain an elevated temperature while mixing and processing the composition.

The gel form antiperspirant stick compositions of the present invention are used in a conventional manner. Specifically, the compositions may be used to prevent and/or control perspiration wetness by topically applying, one or more times a day, an effective amount of the composition to areas of the body particularly prone to perspiration (e.g., the underarm or axillary area).

The following non-limiting examples illustrate the compositions, methods of making, and methods of use described in the present application.

EXAMPLES I–III

Opaque antiperspirant gel stick compositions are exemplified in these examples. The compositions are made according to the following procedure.

Phase A - Weigh the water into a beaker. Add the sodium benzoate or sodium octanoate and agitate at room temperature until dissolved, to form a gel stabilizer solution.

Add the gel stabilizer solution and the Phase A solvents (the Phase A portion of the dipropylene glycol, propylene glycol, and 3-methyl-2-oxazolidinone, as applicable) into a 3-neck round bottom flask equipped with a reflux condenser, thermometer, and magnetic stir bar. Place the flask in a heating mantle connected to a rheostat.

Weigh the gelling agent and add it to the flask. Heat the flask while stirring until the gelling agent is completely dissolved at about 110° C. to about 132 ° C. for Example I, at about 120° C. to about 142° C. for Example II, and at about 90° C. to about 110° C. for Example III. Hold within the applicable temperature range with stirring.

Phase B - Weigh the Phase B portion of the dipropylene glycol and the ethanol into a round bottom flask equipped with a reflux condenser, thermometer, and mechanical stirrer. Add the antiperspirant active and mix until well dispersed. Mixing can alternately be performed with a high shear mixer. As applicable, add the fumed silica, fumed aluminum oxide, and sodium sebacate to the flask, place the flask in a heating mantle connected to a rheostat, and heat the flask while stirring to about 65° C. to about 90° C. for Example I, about 70° C. to about 95° C. for Example II, and about 45° C. to about 70° C. for Example III. Hold within the applicable temperature range with stirring.

Add Phase B to Phase A flask and mix until homogenous. Pour mixture into cannister(s) and cover loosely to contain volatile materials. Allow composition to cool to room temperature.

| Ingredients | Example # (Weight %) | | |
|---|---|---|---|
| | I | II | III |
| Phase A | | | |
| Sodium Benzoate | 1.00 | — | 2.00 |
| Sodium Octanoate | — | 1.00 | — |
| Water | 2.00 | 2.00 | 2.00 |
| Dipropylene Glycol | 15.00 | — | 41.50 |
| Propylene Glycol | 15.00 | 42.00 | — |
| 3-Methyl-2-Oxazolidinone | 10.00 | — | 5.00 |
| Di(m-fluorobenzylidene) Sorbitol | 3.00 | 3.00 | — |
| Dibenzylidene Sorbitol (unsubstituted) | — | — | 3.50 |
| Phase B | | | |
| Dipropylene Glycol | 27.00 | 30.00 | 20.00 |
| Ethanol | 10.00 | — | 10.00 |
| Zirconium Aluminum Trichlorohydrex Gly (ZAG)* | 15.00 | 15.00 | 15.00 |
| Fumed Silica** | 1.67 | 1.00 | 1.00 |
| Fumed Aluminum Oxide*** | 0.30 | — | — |
| Diethyl Sebacate | — | 5.0 | — |

*Available as WESTCHLOR ZR 30B DM Powder from Westwood Chemical Corp. (Middletown, NY, U.S.A.).
**Available as CABOSIL from Cabot Corp. (Tuscola, IL, U.S.A.).
***Available as Aluminum Oxide C from Deguss, Inc. (Teterboro, NJ, U.S.A.).

The opaque sticks have excellent gel properties, are storage stable and provide excellent antiperspirant efficacy when applied to the axillary area.

EXAMPLES IV–VI

Clear antiperspirant gel stick compositions are exemplified in these examples. The compositions are made according to the following procedure.

Phase A - Weigh the Phase A portion of the water into a beaker. Add the gel stabilizer and agitate at room temperature until dissolved, to form a gel stabilizer solution.

Add the gel stabilizer solution and the remaining Phase A solvents, as applicable into a 3-neck round bottom flask equipped with a reflux condenser, thermometer, and magnetic stir bar. Place the flask in a heating mantle connected to a rheostat.

Weigh the gelling agent and add it to the flask. Heat the flask while stirring until the gelling agent is completely dissolved at about 110° C. to about 132° C. for Example IV, at about 120° C. to about 142° C. for Example V, and at about 90° C. to about 110° C. for Example VI. Hold within the applicable temperature range with stirring.

Phase B - Weigh the propylene glycol into a flask. Add the antiperspirant active and mix until homogenous. Add the Phase B portion of the water. Mix with a high energy mixer and heat to about 45° C. to about 85° C. while mixing until the active is solubilized. Deaerate.

Add solubilized active, and the ethanol and silica, as applicable, into a round bottom flask equipped with a reflux condenser, thermometer, and magnetic stir bar. Place the flask in a heating mantle connected to a rheostat, and heat the flask while stirring to about 65° C. to about 90° C. for Example IV, about 70° C. to about 95° C. for Example V, and about 45° C. to about 70° C. for Example VI. Hold within the applicable temperature range with stirring.

Add Phase B to Phase A flask and mix until homogenous. Pour mixture into cannister(s) and cover loosely to contain volatile materials. Allow composition to cool to room temperature. The composition will be clear or translucent.

| Ingredients | Example # (Weight %) | | |
|---|---|---|---|
| | IV | V | VI |
| Phase A | | | |
| Sodium Benzoate | 1.00 | — | 2.00 |
| Sodium Octanoate | — | 1.00 | — |
| Water | 2.00 | 2.00 | 2.00 |
| Dipropylene Glycol | 43.00 | — | 46.50 |
| Propylene Glycol | — | 59.00 | — |
| 3-Methyl-2-Oxazolidinone | 10.00 | — | 5.00 |
| Diethyl Sebacate | — | 5.00 | — |
| Di(m-fluorobenzylidene) Sorbitol | 3.00 | 3.00 | — |
| Dibenzylidene Sorbitol (unsubstituted) | — | — | 3.50 |
| Phase B | | | |
| Ethanol | 10.00 | — | 10.00 |
| Propylene Glycol | 15.00 | 15.00 | 15.00 |
| Aluminum Chlorohydrate* | 13.50 | 13.50 | 13.50 |
| Fumed Silica** | 1.00 | — | 1.00 |
| Water | 1.50 | 1.50 | 1.50 |

*Available as WESTCHLOR DM 200 Powder from Westwood Chemical Corp. (Middletown, NY, U.S.A.).
**Available as CABOSIL from Cabot Corp. (Tuscola, IL, U.S.A.).

The sticks have excellent gel properties, are storage stable, and provide excellent antiperspirant efficacy when applied to the axillary area.

What is claimed is:

1. A solid antiperspirant composition in gel stick form, having an acidic pH, comprising:
   (a) from about 0.5% to about 35% of an antiperspirant active;
   (b) from about 0.5% to about 10% of a gelling agent which is a dibenzylidene alditol or a mixture of dibenzylidene alditols;
   (c) from about 5% to about 98% of a solvent for said gelling agent; and
   (d) from about 0.05% to about 5%, by weight, of a gelling agent stabilizer, said stabilizer being a basic metallic salt of an acid having a pKa of from about 3.8 to about 6.5 at ambient temperature, said salts being at least partially soluble in the composition, and said stabilizer being selected from the group consisting of $C_4$–$C_6$ alkyl dicarboxylate, $C_4$–$C_8$ alkyl monocarboxylate, unsubstituted benzoate, and mono-halogen-, mono-, di-, and tri-hydroxy-, methyl-, ethyl-, and mono- and di-methoxy-substituted benzoate, wherein said gelling agent stabilizer does not contain amino or amido functionalities.

2. A solid antiperspirant according to claim 1, wherein stabilizer is present at a level of from about 0.1% to about 3%.

3. A solid antiperspirant according to claim 1, wherein said stabilizer is a salt selected from the group consisting of unsubstituted benzoates, mono-halogen-, mono-, di-, and ti-hydroxy-, methyl-, ethyl-, and mono- and di-methoxy-, substituted benzoates, succinate, glutarate, adipate, hexanoate, heptanoate, and octanoate salts, and mixtures thereof.

4. A solid antiperspirant according to claim 3, wherein said stabilizer comprises a salt selected from the group consisting of unsubstituted benzoate, octanoate, and succinate salts, and mixtures thereof.

5. A solid antiperspirant composition according to claim 1 wherein said dibenzylidene alditol is selected from the group consisting of dibenzylidene sorbitols, dibenzylidene xylitols, dibenzylidene ribitols, and mixtures thereof.

6. A solid antiperspirant composition according to claim 5 wherein the gelling agent is a dibenzylidene sorbitol.

7. A solid antiperspirant composition according to claim 6 wherein the gelling agent is di(meta-fluorobenzylidene) sorbitol or di (meta-chlorobenzylidene), or a mixture thereof.

8. A solid antiperspirant composition according to claim 6, wherein the gelling agent is unsubstituted dibenzylidene sorbitol.

9. A solid antiperspirant composition according to claim 5 wherein the solvent comprises a monohydric or polyhydric alcohol, or a mixture thereof.

10. A solid antiperspirant composition according to claim 9 wherein the solvent is selected from the group consisting of propylene glycol, dipropylene glycol, tripropylene glycol, triethylene glycol, hexylene glycol, and mixtures thereof.

11. A solid antiperspirant according to claim 9, wherein stabilizer is present at a level of from about 0.1% to about 3%.

12. A solid antiperspirant according to claim 11, wherein said stabilizer is a salt selected from the group consisting of unsubstituted benzoates, mono-halogen-, mono-, di-, and tri-hydroxy-, methyl-, ethyl-, and mono- and di-methoxy-substituted benzoates, succinate, glutarate, adipate, hexanoate, heptanoate, and octanoate salts, and mixtures thereof.

13. A solid antiperspirant according to claim 12, wherein said stabilizer is a salt selected from the group consisting of unsubstituted benzoate succinate, and octanoate salts, and mixtures thereof.

14. A solid antiperspirant composition according to claim 9 wherein the antiperspirant active is in solubilized form.

15. A solid antiperspirant composition according to claim 9 wherein the antiperspirant active is in particulate form.

16. A solid antiperspirant composition according to claim 1, comprising from about 5% to about 35% of said antiperspirant active, from about 2% to about 5% of said gelling agent wherein said gelling agent is a dibenzylidene sorbitol, or mixture thereof, from about 60% to about 80% of said solvent wherein said solvent comprises monohydric or polyhydric alcohol, or a mixture thereof, and from about 0.1% to about 3% of said stabilizer.

17. A solid antiperspirant composition according to claim 1, further comprising from about 0.5% to about 40% of a 2-oxazolidinone compound having a $C_1$–$C_4$ alkyl substituent at the 3 position of the heterocyclic ring, or a mixture thereof.

18. A solid antiperspirant composition according to claim 16, comprising from about 5% to about 15% of 3-($C_1$–$C_2$ alkyl)-2-oxazolidinone, or a mixture thereof.

19. A method for preventing and controlling perspiration wetness in humans comprising the application to the underarm area of an effective amount of the solid antiperspirant composition according to claim 1.

20. An improved process for making an antiperspirant gel stick composition, having acidic pH, containing a solvent, dibenzylidene alditol gelling agent, and an antiperspirant active, said process comprising solubilizing said gelling agent in said solvent at elevated temperature to form a solution and subsequently cooling the solution to form a gel, wherein the improvement comprises incorporating into said solvent an effective amount of a gelling agent stabilizer for enhancing gelling agent stability, said gelling agent stabilizer being a salt of an acid having pKa of from about 3.8 to about 6.5 at ambient temperature, said salt being selected from the group consisting of $C_4$–$C_6$ alkyl dicarboxylates, $C_6$–$C_8$ alkyl monocarboxylates, unsubstituted benzoates, and mono-halogen-, mono-, di-, and tri-hydroxy-, methyl-, ethyl-, and mono- and di-methoxy-substituted benzoates, and mixtures thereof, wherein said gelling agent stabilizer does not contain amino or amido functionalities.

21. A process for making an antiperspirant gel stick composition, having acidic pH, comprising:

(a) preparing a solution containing from about 0.5% to about 10%, by weight of the final composition, of a dibenzylidene alditol gelling agent, a solvent for said gelling agent, and from about 0.05% to about 5%, by weight of the final composition, of a gelling agent stabilizer, said stabilizer being at least partially soluble in said solution, and being a salt of an acid having pKa of from about 3.8 to about 6.5 at ambient temperature, said salt being selected from the group consisting of $C_4$–$C_6$ alkyl dicarboxylates, $C_6$–$C_8$ alkyl monocarboxylates, unsubstituted benzoates, and mono-halogen-, mono-, di-, and tri-hydroxy, methyl, ethyl, and mono- and di-methoxy substituted benzoates, and mixtures thereof, wherein said gel stabilizer does not contain amino or amido functionalities;

(b) mixing an antiperspirant active into said solution; and (c) cooling said solution to form a gel; wherein said gel has an average penetration value of from about 60 to about 200 tenths of a millimeter at ambient temperature.

22. The antiperspirant gel stick made according to the process of claim 20.

23. The antiperspirant gel stick made according to the process of claim 21.

* * * * *

UNITED STATES PATENT AND TRADEMARK OFFICE
CERTIFICATE OF CORRECTION

PATENT NO. : 5,346,694

DATED : September 13, 1994

INVENTOR(S) : Prem S. Juneja

It is certified that error appears in the above-identified patent and that said Letters Patent is hereby corrected as shown below:

Title page, item [56]

In References Cited, Foreign Patent Documents section, "0286522 12/1988 Japan....." should read --0286522 12/1988 Europe.....--.

At Column 8, line 53 "Example" should read --Examples--.

At Column 14, line 41 "substitut d" should read --substituted and--.

At Column 16, Examples I-III footnote *** "Deguss" should read --Degussa--.

Signed and Sealed this

Fourteenth Day of January, 1997

Attest:

BRUCE LEHMAN

Attesting Officer

Commissioner of Patents and Trademarks